US010065938B2

(12) United States Patent
Izawa et al.

(10) Patent No.: US 10,065,938 B2
(45) **Date of Patent: *Sep. 4, 2018**

(54) METHOD FOR PRODUCING HYDRIDE USING UNSATURATED COMPOUND HAVING CARBON NUMBER OF 4 AS RAW MATERIAL

(71) Applicant: MITSUBISHI CHEMICAL CORPORATION, Chiyoda-ku (JP)

(72) Inventors: Yusuke Izawa, Mie (JP); Masaru Utsunomiya, Tokyo (JP); Norikazu Konishi, Mie (JP); Kouta Tanaka, Mie (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/190,244

(22) Filed: Jun. 23, 2016

(65) Prior Publication Data

US 2016/0297786 A1 Oct. 13, 2016

Related U.S. Application Data

(63) Continuation of application No. 14/161,081, filed on Jan. 22, 2014, now Pat. No. 9,522,897, which is a continuation of application No. PCT/JP2012/068379, filed on Jul. 19, 2012.

(30) Foreign Application Priority Data

Jul. 20, 2011 (JP) ................................ 2011-159105
Jul. 28, 2011 (JP) ................................ 2011-165937
Nov. 2, 2011 (JP) ................................ 2011-241574

(51) Int. Cl.

*C07D 307/20* (2006.01)
*C07C 29/17* (2006.01)
*B01J 21/08* (2006.01)
*B01J 23/44* (2006.01)
*B01J 23/755* (2006.01)
*B01J 23/86* (2006.01)
*B01J 35/00* (2006.01)
*B01J 35/02* (2006.01)
*C07C 45/62* (2006.01)
*C07C 45/86* (2006.01)
*C07C 29/94* (2006.01)

(52) U.S. Cl.

CPC ............ *C07D 307/20* (2013.01); *B01J 21/08* (2013.01); *B01J 23/44* (2013.01); *B01J 23/755* (2013.01); *B01J 23/866* (2013.01); *B01J 35/0006* (2013.01); *B01J 35/02* (2013.01); *C07C 29/172* (2013.01); *C07C 29/94* (2013.01); *C07C 45/62* (2013.01); *C07C 45/86* (2013.01)

(58) Field of Classification Search

CPC . B01J 21/08; B01J 23/44; B01J 23/755; B01J 23/866; B01J 35/0006; B01J 35/02; C07C 29/172; C07C 29/94; C07C 45/62; C07C 45/86; C07C 307/20

See application file for complete search history.

(56) References Cited

U.S. PATENT DOCUMENTS 3,715,404 A * 2/1973 Lindlar .................... B01J 23/40 502/168
4,544,767 A 10/1985 Cowan
4,864,066 A * 9/1989 Mueller ................ C07C 29/172 568/861
5,319,111 A 6/1994 Zimmermann et al.
5,905,159 A 5/1999 Fischer et al.
6,387,224 B1 5/2002 Pinkos et al.
7,371,908 B2 * 5/2008 Koch ........................ C07C 5/03 585/266
9,522,897 B2 * 12/2016 Izawa .................. C07C 29/172
2009/0171037 A1 7/2009 Aoshima et al.

FOREIGN PATENT DOCUMENTS

JP 52-007909 1/1977
JP 61-097235 4/1986
JP 61-171447 8/1986
JP 61-197534 A 9/1986
JP 62-4172 1/1987

(Continued)

OTHER PUBLICATIONS

Mcdonald et al., "Total Synthesis of (−)-Histrionicotoxin 285A and (−)-Perhydrohistrionicotoxin," Org. Lett. 2008, 10(19) 4227-4229.*
International Search Report dated Oct. 2, 2012 in PCT/JP2012/068379 filed Jul. 19, 2012.
Journal of Catalysis, 2004, vol. 227, No. 2, p. 428-435.
Catalysis Today, 2005, vol. 100, No. 3-4, p. 467-471.
Macdonald, "Total Synthesis of (−)-Histrionicotoxin 285A and (−)-Perhydrohistorionicotoxin," Organic Letters, 20(19), 4227-4229, 2008.
Japanese Office Action as received in the corresponding Patent Application No. 2012-160616 dated Nov. 17, 2015 w/English Translation.

(Continued)

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

The present invention relates to a method for producing a hydride having a carbon number of 4, comprising contacting, in liquid phase, an unsaturated compound having a carbon number of 4 as a raw material with a solid catalyst obtained by loading a metal element belonging to Groups 9 to 11 of the long periodic table on a support, thereby performing hydrogenation to produce a corresponding hydride having a carbon number of 4, wherein hydrogenation is performed in the presence of, as a solvent, a 1,4-butanediol having a nitrogen component concentration of 1 ppm by weight to 1 wt % in terms of nitrogen atom.

18 Claims, No Drawings

(56) References Cited

FOREIGN PATENT DOCUMENTS

| | | | |
|---|---|---|---|
| JP | 62-4174 | B2 | 1/1987 |
| JP | 01-168345 | | 7/1989 |
| JP | 01-168346 | | 7/1989 |
| JP | 07-082187 | | 3/1995 |
| JP | 10-265418 | | 10/1998 |
| JP | 11-502811 | | 3/1999 |
| JP | 2930141 | | 5/1999 |
| JP | 11-228468 | | 8/1999 |
| JP | 11-228468 | A | 8/1999 |
| JP | 2000-507566 | | 6/2000 |
| JP | 2003-26622 | A | 1/2003 |
| JP | 2008-101143 | A | 5/2008 |

OTHER PUBLICATIONS

Japanese Office Action as received in the corresponding Patent Application No. 2012-160731 dated Nov. 17, 2015 w/English Translation.

Office Action dated Jun. 14, 2016 in Japanese Patent Application No. 2012-160731 (with English language translation).

* cited by examiner

METHOD FOR PRODUCING HYDRIDE USING UNSATURATED COMPOUND HAVING CARBON NUMBER OF 4 AS RAW MATERIAL

This application is a continuation of U.S. application Ser. No. 14/161,081 filed Jan. 22, 2014, pending, which is a continuation of PCT/JP2012/068379 filed Jul. 19, 2012 and claims the benefit of JP 2011-159105 filed Jul. 20, 2011, JP 2011-165937 filed Jul. 28, 2011 and JP 2011-241574 filed Nov. 2, 2011.

TECHNICAL FIELD

The present invention relates to a method for producing a hydride having a carbon number of 4 by using, as a raw material, an unsaturated compound having a carbon number of 4. More specifically, the present invention relates to a method for producing a corresponding hydride having a carbon number of 4 by bringing an unsaturated compound having a carbon number of 4 into contact with a solid catalyst in liquid phase.

BACKGROUND ART 1,4-Butanediol (hereinafter, sometimes simply referred to as "1,4BG") is known to be a very useful substance used as a raw material of various solvents or derivatives. Conventionally, a variety of methods for industrially producing 1,4BG have been developed and, for example, there are known a method of performing an acetoxylation reaction by using butadiene as a raw material and using the raw material butadiene, acetic acid and oxygen to obtain diacetoxybutene that is an intermediate, and hydrogenating and hydrolyzing the diacetoxybutene to produce 1,4BG (Patent Document 1), a method for obtaining a 1,4BG-containing crude hydrogenation product by using maleic acid, succinic acid, maleic anhydride and/or fumaric acid as raw materials and hydrogenating them (Patent Document 2), and a method for producing 1,4BG by hydrogenating butynediol that is obtained by using acetylene as a raw material and contacting it with an aqueous formaldehyde solution (Patent Document 3).

In such a process for producing 1,4BG, it is known that an unsaturated compound having a carbon number of 4 occurs as a byproduct. For example, in the production by an acetoxylation reaction of butadiene, 1,4-diacetoxy-2-butene, 1-acetoxy-4-hydroxy-2-butene, 1,4-dihydroxy-2-butene or the like occurs as a byproduct. Furthermore, in the case of the production method by hydrogenation of maleic acid or the like, gamma butyrolactone is produced. Also in the case of using acetylene as a raw material, 1,4-dihydroxy-2-butyne, 1,4-dihydroxy-2-butene or the like occurs as a byproduct. These unsaturated compounds may be separated directly by a distillation column, but the step for separation can be omitted by performing a hydrogenation reaction to convert those compounds into a different compound easily separable from 1,4BG and thereafter, separating the compound by distillation or the like or converting it into 1,4BG.

Various catalysts for use in such a hydrogenation reaction are present, and as regards the catalyst capable of suppressing reduction in the selectivity due to a byproduct at the hydrogenation, for example, Patent Document 4 has reported that the amount of byproduct butyl acetate can be reduced by performing hydrogenation of 1,4-diacetoxy-2-butene in the presence of an alkali metal or alkaline earth metal of acetic acid. Also, Patent Document 5 has reported that an effect of improving the reaction rate is obtained by allowing an amine to exist at the time of hydrogenating octadienols by a solid catalyst.

BACKGROUND ART DOCUMENT

Patent Document

Patent Document 1: JP-A-52-7909 (the term "JP-A" as used herein means an "unexamined published Japanese patent application")

Patent Document 2: Japanese Patent No. 2,930,141

Patent Document 3: JP-B-62-4172 (the term "JP-B" as used herein means an "examined Japanese patent publication")

Patent Document 4: U.S. Pat. No. 4,544,767

Patent Document 5: JP-A-11-228468

SUMMARY OF INVENTION

Problem that Invention is to Solve

Reduction in the hydrogenation rate due to catalyst deterioration during a hydrogenation reaction using the catalysts of Patent Documents 4 and 5 can be partially compensated for by raising the temperature, but in the case of continuously producing a hydride, the life of catalyst needs to be enhanced, and the formulation for improving the catalyst life has not been heretofore specifically studied.

An object of the present invention is to provide an industrially useful method for producing a hydride, wherein continuously producing a corresponding hydride having a carbon number of 4 by contacting, in liquid phase, an unsaturated compound having a carbon number of 4 with a solid catalyst that is obtained by loading a metal element belonging to Groups 9 to 11 of the periodic table on a support, the catalyst deterioration can be reduced and at the same time, the catalyst life can be extended.

Means for Solving Problem

As a result of intensive studies to attain the above-described object, the present inventors have found that when a hydrogenation reaction is performed by incorporating a specific amount of a nitrogen component usually known as a component accelerating the catalyst deterioration of a hydrogenation catalyst into 1,4BG that is a solvent, this is effective in improving the catalyst life. Above all, the effect is remarkable on a solid catalyst containing a metal element belonging to Groups 9 to 11 of the periodic table. The gist of the present invention resides in the following (1) to (5).

(1) A method for producing a hydride having a carbon number of 4, comprising contacting, in liquid phase, an unsaturated compound having a carbon number of 4 as a raw material with a solid catalyst obtained by loading a metal element belonging to Groups 9 to 11 of the long periodic table on a support, and performing hydrogenation to continuously produce a corresponding hydride having a carbon number of 4, wherein the hydrogenation is performed in the presence of, as a solvent, 1,4-butanediol having a nitrogen component concentration of 1 ppm by weight to 1 wt % in terms of nitrogen atom.

(2) The method for producing a hydride having a carbon number of 4 described in the above (1), wherein the 1,4-butanediol is previously contacted with an anion exchange resin to adjust the nitrogen concentration in the 1,4-butanediol to be from 1 ppm by weight to 1 wt %.

(3) The method for producing a hydride having a carbon number of 4 described in the above (1) or (2), wherein the support is at least one member of silica and diatomaceous earth.

(4) The method for producing a hydride having a carbon number of 4 described in any one of the above (1) to (3), wherein the unsaturated compound having a carbon number of 4 is 1,4-dihydroxy-2-butene and the corresponding hydride having a carbon number of 4 is at least one member of 2,-hydroxytetrahydrofuran and 1,4-butanediol.

(5) A method for producing 1,4-butanediol comprising flowing crude 1,4-butanediol containing an unsaturated compound having a carbon number of 4 into a packed bed filled with a solid catalyst obtained by loading a metal element belonging to Groups 9 to 11 of the long periodic table on a support, and converting the unsaturated compound having a carbon number of 4 into a corresponding hydride having a carbon number of 4 to obtain 1,4-butanediol reduced in the concentration of an unsaturated compound having a carbon number of 4, wherein the concentration of a nitrogen component contained in the crude 1,4-butanediol in the packed bed is from 1 ppm by weight to 1 wt % in terms of nitrogen atom.

Advantageous Effects of Invention

According to the present invention, at the time of producing a hydride by continuously hydrogenating an unsaturated compound having a carbon number of 4, deterioration of a hydrogenation catalyst due to a continuous operation can be suppressed, and the life of a hydrogenation catalyst in a continuous operation can be improved.

Mode for Carrying Out Invention

The present invention is described in detail below.

The unsaturated compound having a carbon number of 4 for use in the present invention includes, for example, a compound containing a carbon-carbon double bond and/or a carbon-oxygen double bond and having a carbon number of 4. Examples thereof include olefins containing a carbon-carbon double bond, aldehydes containing a carbon-oxygen double bond, ketones, and esters, where the number of carbon atoms constituting the compound is 4. Other examples include unsaturated aldehydes, unsaturated ketones, and unsaturated esters which contain both a carbon-carbon double bond and a carbon-oxygen double bond in the same molecule. Specific examples of these compounds include 1-butene, 2-butene, butadiene, normal-butylaldehyde, isobutylaldehyde, crotonaldehyde, methacrolein, 2-hydroxybutanal, 3-hydroxybutanal, 4-hydroxybutanal, 2-oxobutanal, 3-oxobutanal, methyl ethyl ketone, methyl vinyl ketone, 1-hydroxyethyl methyl ketone, 2-hydroxyethyl methyl ketone, 1-butenol, 2-butenol, 2-hydroxy-3-butenol, 1,4-dihydroxy-2-butene, 3,4-dihydroxy-1-butene, gamma butyrolactone, furfural, furfuryl alcohol, 2,3-dihydrofuran, 2,5-dihydrofuran, and furan.

In the present invention, at the time of hydrogenating an unsaturated compound having a carbon number of 4 in liquid phase, 1,4BG is caused to exist as a solvent. The amount of 1,4BG used as a solvent is not particularly limited. The method for allowing 1,4BG as a solvent to exist together with an unsaturated compound having a carbon number of 4 of the raw material is not particularly limited, and this can be attained by mixing commercially available 1,4BG with an unsaturated compound having a carbon number of 4 of the raw material.

Also, as the solvent 1,4BG, for example, 1,4BG produced by performing a diacetoxylation reaction of butadiene in the presence of acetic acid and oxygen to obtain a solution containing 1,4-diacetoxy-2-butene, and performing hydrogenation and hydrolysis thereof may be used. Most commonly, butadiene, acetic acid and oxygen are reacted to obtain 1,4-diacetoxy-2-butene and 3,4-diacetoxy-1-butene which are a diacetoxyallyl compound, and at this time, an unsaturated compound having a carbon number of 4, such as 1-hydroxy-4-acetoxy-2-butene, 3-hydroxy-4-acetoxy-1-butene and 4-hydroxy-3-acetoxy-1-butene which are a hydrolysate of those diacetoxyallyl compounds, is produced in combination. The thus-obtained 1,4BG containing an unsaturated compound having a carbon number of 4 may also be used directly as the unsaturated compound having a carbon number of 4 of the raw material and as the solvent 1,4BG for use in the present invention. Furthermore, as for the byproduct during the acetoxylation reaction, a slight amount of a compound containing a carbon-carbon double bond and/or a carbon-oxygen double bond and having a carbon number of 4, such as 2-hydroxyethyl methyl ketone, also occurs as a byproduct.

As the catalyst for use in the diacetoxylation reaction of butadiene, any catalyst may be used as long as it has the capability of converting butadiene to 1,4-diacetoxy-2-butene, but a solid catalyst containing a transition metal of Groups 8 to 10 of the long periodic table (hereinafter, unless otherwise indicated, the "periodic table" indicates the long periodic table) is preferred, and a palladium solid catalyst is more preferred. The palladium solid catalyst is composed of a palladium metal or a salt thereof, and the co-catalyst used is preferably a metal such as bismuth, selenium, antimony, tellurium and copper, or a salt thereof, more preferably tellurium. The combination of palladium and tellurium is preferred because of high catalytic activity and high selectivity of a diacetoxyallyl compound. Therefore, the catalyst is preferably a solid catalyst where palladium and tellurium are supported as active ingredients.

The solvent 1,4BG can also be produced by a production method other than the acetoxylation of butadiene.

The concentration of the unsaturated compound having a carbon number of 4 of the present invention in the solvent 1,4BG is preferably from 0.01 to 50 wt %, more preferably from 0.1 to 30 wt %, still more preferably from 0.5 to 20 wt %. There is a tendency that as this concentration is higher, the load of hydrogenation step increases and the amount of catalyst becomes significantly large.

The corresponding hydride having a carbon number of 4 obtained by hydrogenating an unsaturated compound having a carbon number of 4 of the raw material is, for example, butane, 1-butanol, isobutanol, 1,2-butanediol, 1,3-butanediol, 1,4-butanediol, 2-butanol, or tetrahydrofuran.

In the present invention, it is preferred that the unsaturated compound having a carbon number of 4 is 1,4-dihydroxy-2-butene and at the same time, the corresponding hydride having a carbon number of 4 is at least one of 2-hydroxytetrahydrofuran and 1,4-butanediol The solvent 1,4BG for use in the present invention may be sufficient if it contains 1,4-butanediol as a main component, and specifically, the concentration of 1,4-butanediol is from 50 to 99.99 wt %, preferably from 60 to 95 wt %, more preferably from 70 to 90 wt %. Also, this solvent may contain water. As the 1,4BG concentration is higher, the effect of hydrogenation tends to decrease, and as the 1,4BG concentration is lower, the effect of improving the catalyst life of hydrogenation catalyst by a nitrogen component decreases.

In the present invention, it is essential for the solvent 1,4BG to contain a nitrogen component. The concentration of the nitrogen component in the solvent 1,4BG is, in terms of nitrogen atom, preferably from 1 ppm by weight to 1 wt %, more preferably from 2 ppm by weight to 0.1 wt %, still more preferably from 3 to 500 ppm by weight. If the nitrogen atom concentration exceeds this range, the effect on the acceleration of deterioration rate becomes greater than on the improvement of catalyst life, and if the concentration is less than the range above, the effect of improving the catalyst life is scarcely brought out.

The present invention is effective particularly when an acidic component is present in at least either one of the unsaturated compound having a carbon number of 4 and the solvent 1,4BG. Representative acidic components include a chlorine-containing compound such as hydrochloric acid, a sulfur-containing compound, such as sulfuric acid and sulfonic acid, and a carboxylic acid such as formic acid and acetic acid. Such an acid component sometimes affects the catalyst deterioration even with an amount near the detection limit.

The nitrogen component is in particular preferably an eluted substance from a nitrogen component-containing anion exchange resin.

In addition, it is also preferred that 1,4-butanediol of the present invention contains a nitrogen-containing compound represented by the following formula (1):

[Chem. 1]

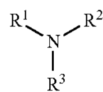

(1)

In formula (1), each of $R^1$ to $R^3$ independently represents a hydrogen atom, an alkyl group, an alkenyl group, an aryl group, an alkoxy group, a hydroxy group, an amino group, an alkylthio group or an arylthio group, and these groups may further have a substituent. This substituent may contain a heteroatom. $R^1$ to $R^3$ may be the same as or different from each other but a case where all of $R^1$ to $R^3$ are a hydrogen atom is excluded.

Also, in formula (1), from the standpoint of suppressing catalyst deterioration and increasing the basicity, each of $R^1$ to $R^3$ is independently preferably a hydrogen atom, an alkyl group, an aryl group or an amino group. In this case, $R^1$ to $R^3$ may be the same as or different from each other but a case where all of $R^1$ to $R^3$ are a hydrogen atom is excluded.

The alkyl group is a chain (linear or branched) alkyl group or a cyclic alkyl group. The chain alkyl group is usually an alkyl group having a carbon number of 1 to 20, preferably from 1 to 12, and specific examples thereof include a methyl group, an ethyl group, an n-propyl group, an i-propyl group, an n-butyl group, an i-butyl group, a sec-butyl group, a tert-butyl group, a pentyl group, a hexyl group, an octyl group, and a decyl group. The cyclic alkyl group is usually an alkyl group having a carbon number of 3 to 20, preferably from 4 to 11, and specific examples thereof include a cyclopentyl group, a cyclohexyl group, an a cyclooctyl group. The substituent which may be substituted on the alkyl group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

The alkenyl group is a chain (linear or branched) alkenyl group or a cyclic alkenyl group. The chain alkenyl group has a carbon number of usually from 1 to 20, preferably from 1 to 12, and specific examples thereof include an ethenyl group, a 1-propenyl group, an isopropenyl group, a 2-butenyl group, a 1,3-butadienyl group, a 2-pentenyl group, and a 2-hexenyl group. The cyclic alkenyl group has a carbon number of usually from 3 to 20, preferably from 4 to 11, and specific examples thereof include a cyclopropenyl group, a cyclopentenyl group, and a cyclohexenyl group. The substituent which may be substituted on the alkenyl group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

Examples of the aryl group include a phenyl group, a benzyl group, a mesityl group, a naphthyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, an isoxazolyl group, an isothiazolyl group, an imidazolyl group, an oxazolyl group, a thiazolyl group, a thiadiazolyl group, a thienyl group, a thiophenyl group, a triazolyl group, a tetrazolyl group, a pyridyl group, a pyrazinyl group, a pyrimidinyl group, a pyridazinyl group, a pyrazolyl group, a pyrrolyl group, a pyranyl group, a furyl group, a furazanyl group, an imidazolidinyl group, an isoquinolyl group, an isoindolyl group, an indolyl group, a quinolyl group, a pyridothiazolyl group, a benzimidazolyl group, a benzoxazolyl group, a benzothiazolyl group, a benzotriazolyl group, a benzofuranyl group, an imidazopyridinyl group, a triazopyridinyl group, an a purinyl group. The aryl group has a carbon number of usually from 5 to 20, preferably from 5 to 12, and encompasses a heteroaryl group containing oxygen, nitrogen, sulfur or the like. The substituent which may be substituted on the aryl group is not particularly limited as long as it does not seriously inhibit the effects of the present invention, but examples thereof include an alkyl group having a carbon number of 1 to 10, an acyl group having a carbon number of 1 to 10, an alkoxy group having a carbon number of 1 to 10, a cycloalkyl group having a carbon number of 1 to 10, an aryl group having a carbon number of 6 to 10, an aryloxy group having a carbon number of 6 to 10, an alkylaryl group having a carbon number of 7 to 12, an alkylaryloxy group having a carbon number of 7 to 12, an arylalkyl group having a carbon number of 7 to 12, an arylalkoxy group having a carbon number of 7 to 12, and a hydroxy group. Also, the substituent may contain a heteroatom such as oxygen, nitrogen, sulfur and phosphorus.

Specific examples of the aryl group include a phenyl group, a benzyl group, a mesityl group, a naphthyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, a 2-isopropylphenyl group, a 2-tert-butylphenyl group, a 2,4-di-tert-butylphenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group, a 4-trifluoromethylphenyl group, a 2-methoxyphenyl group, a 3-methoxyphenyl group, a 4-methoxyphenyl group, a 3,5-dimethoxyphenyl group, a 4-cyanophenyl group, a 4-nitrophenyl group, a 4-aminophenyl group, a trifluoromethylphenyl group, and a pentafluorophenyl group.

The alkoxy group has a carbon number of usually from 1 to 20, preferably from 1 to 12, and specific examples thereof include a methoxy group, an ethoxy group, a butoxy group, and a phenoxy group. The substituent which may be substituted on the alkoxy group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used.

Also, the substituent may contain a heteroatom such as oxygen, nitrogen, sulfur and phosphorus.

The amino group has a carbon number of usually from 0 to 20, preferably from 0 to 12. Specific examples thereof include a methylamino group, an ethylamino group, a propylamino group, a butylamino group, a dimethylamino group, a diethylamino group, an anilino group, a toluidino group, an anisidino group, a diphenylamino group, and an N-methyl-N-phenylamino group. The substituent which may be substituted on the amino group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

The alkylthio group has a carbon number of usually from 1 to 20, preferably from 1 to 12. Specific examples thereof include a methylthio group, an ethylthio group, a propylthio group, and an isopropylthio group. The substituent which may be substituted on the alkylthio group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

The arylthio group has a carbon number of usually from 6 to 20, preferably from 6 to 12. Specific examples thereof include a phenylthio group and a tolylthio group. The substituent which may be substituted on the arylthio group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

Furthermore, in formula (1), $R^1$ and $R^2$, $R^2$ and $R^3$, or $R^3$ and $R^1$ may combine with each other to form a ring.

Specifically, for example, in view of basicity and stability in 1,4BG, the compound as above is preferably a primary amine such as octylamine, nonylamine, 1-aminodecane, aniline and phenethylamine, a secondary amine such as dipentylamine, dihexylamine, diheptylamine, dicyclohexylamine and N-methylaniline, a tertiary amine such as tributylamine, tripentylamine and N,N-dimethylaniline, a diamine such as 1,3-propanediamine and N,N-dimethyl-1,6-hexanediamine, a 5-membered ring amine such as N-butylpyrrole, N-butyl-2,3-dihydropyrrole, N-butylpyrrolidine and 2,3-dihydro-1H-indole, a 6-membered ring amine such as 4-aminomethylpiperidine, 4-dimethylaminopyridine, 1,2,3,4-tetrahydroquinoline, 4-amino-5,6-dihydro-2-methylpyrimidine, 2,3,5,6-tetramethylpyrazine and 3,6-dimethylpyridazine, or an eluted matter of an anion exchange resin, and among theses, an eluted matter of an anion exchange resin having a primary amine polyethylene diamine skeleton containing an N—H bond is preferred. The eluted matter from an anion exchange resin is a polyamine. The polyamine is a general term for linear aliphatic hydrocarbons where two or more primary amino groups are connected, and in the present invention, this is a polymer containing two or more, preferably from 3 to 20, constituent units derived from a compound where any one or more of $R^1$ to $R^3$ in the nitrogen-containing compound represented by formula (1) is an alkyl group. Furthermore, the compound containing an oxygen atom is preferably a chain aminoalcohol such as 4-aminobutanol and 2-aminobutanol, or a cyclic amine such as 2-ethylmorpholine, N-methoxycarbonylmorpholine, prolinol, 3-hydroxypiperidine, 4-hydroxypiperidine, tetrahydrofurfurylamine and 3-aminotetrahydropyrane. In view of basicity, a tertiary amine such as tributylamine, tripentylamine and N,N-dimethylaniline, or an eluted matter of an anion exchange resin having a primary amine polyethylenediamine skeleton containing an N—H bond, is more preferred.

In the present invention, as for the nitrogen-containing compound represented by formula (1), one kind of a compound may be contained, or two or more kinds of compounds may be contained.

In addition, it is also preferred for the 1,4-butanediol used in the present invention to contain an amide as a nitrogen-containing compound. Specifically, a carboxylic acid amide is preferably contained. As the carboxylic acid amide, a primary amide, a secondary amide or a tertiary amide can be used, and an N-alkyl substituted amide, an N-alkenyl substituted amide, an N-aryl substituted amide or the like, where the number of substituents of the N-substitution is from 0 to 2, is used. Also, the substituent may contain a heteroatom, and the substituents may be the same as or different from each other. On the other hand, the substituent on the carbonyl side includes, for example, a hydrogen atom, an alkyl group, an alkenyl group, and an aryl group. Furthermore, these substituents may combine with each other to form a ring. From the standpoint that side reaction, decomposition and the like can be suppressed, the substituent on the carbonyl side is preferably an alkyl substituent.

Specifically, preferred compounds as such a compound include amides having a chain skeleton, e.g., acetamide as a primary amide, N-methylacetamide and N-ethylacetamide as a secondary amide, and N,N-dimethylacetamide as a tertiary amide; aromatic amides such as benzamide; and cyclic amides, e.g., 2-pyrrolidone as a secondary amide, and N-methylpyrrolidone, N-ethylpyrrolidone, N-vinylpyrrolidone, 2-piperidone and N-methylpiperidone as a tertiary amide. More preferred compounds include acetamide, N-methylacetamide, 2-pyrrolidone, and N-methylpyrrolidone. Among these, the compound is preferably acetamide, 2-pyrrolidone or N-methylpyrrolidone. Also, the amide used in the present invention may be one kind of an amide or two or more kinds of amides.

The method for causing a nitrogen component to exist in 1,4BG in an amount of 1 ppm by weight to 1 wt % as the concentration in terms of nitrogen atom is not particularly limited but, for example, a method of adding the above-described nitrogen component to commercially available 1,4BG, and a method of previously contacting 1,4BG with an anion exchange resin, are preferred. In the case of eluting an amine component contained in an anion exchange resin into the 1,4BG, the 1,4BG is brought into contact with the anion exchange resin, and the contact form is not particularly limited. Examples include a method of adding an anionic exchange resin to the 1,4BG to elute an amine, and a method of flowing the 1,4BG through a vessel, pipe or the like filled with an anion exchange resin to elute an amine. Among these, from the standpoint that a step of heating the 1,4BG or separating the anion exchange resin after heating can be omitted, it is preferred to elute an amine by flowing the 1,4BG through a vessel, pipe or the like filled with an anion exchange resin, The eluted matter from the anion exchange resin is a polyamine. The polyamine is a general term for linear aliphatic hydrocarbons where two or more primary amino group are connected, and in the present invention, this is a polymer containing two or more, preferably from 3 to 20, constituent units derived from a compound where any one or more of $R^1$ to $R^3$ in the nitrogen-containing compound represented by formula (1) is an alkyl group, The solid catalyst for use in the present invention is obtained by loading a metal element belonging to Groups 9 to 11 of the periodic table, that is, one member or two or more members of cobalt (Co), rhodium (Rh), iridium (Ir), nickel (Ni), palladium (Pd), platinum (Pt), copper (Cu), silver (Ag) and gold (Au), on a support. Among these, a metal element belonging to Group 10 is preferred, and in view of catalyst cost and catalytic activity, nickel is most preferred.

Incidentally, the form of the metal element belonging to Groups 9 to 11 of the periodic table in the solid catalyst may be a metal simple substance or may be an oxide, a hydroxide or other various salts. In the case where the ratio of an oxide or the like for a metal simple substance is high, a treatment for conversion into a metal simple substance may be performed by previously applying a reductive activation treatment with a hydrogen gas before starting the reaction, but the reaction may be started with no treatment. That is, a hydrogen gas is introduced into the hydrogenation reaction system and therefore, such an oxide or the like is reduced to an active metal element during the reaction.

On the other hand, as for the support, the metal element used is preferably supported on a support such as silica, alumina, titania, zirconia, active carbon, graphite and diatomaceous earth, and among these, one member or two or more members of silica, diatomaceous earth and the like may be preferably used. Silica is particularly preferred. The content of the metal element component belonging to Groups 9 to 11 of the periodic table in the solid catalyst (here, when the metal element belonging to Groups 9 to 11 of the periodic table is in the form of a metal oxide or the like, the content of the metal element component belonging to Groups 9 to 11 of the periodic table in the solid catalyst is the content as the metal oxide or the like) is preferably from 5 to 80 wt %, more preferably from 15 to 80 wt %, still more preferably from 50 to 80 wt %.

On the other hand, the content of the support in the solid catalyst is preferably from 5 to 95 wt %, more preferably from 7 to 80 wt %, still more preferably from 10 to 60 wt %.

If the content of the Group 10 metal element component is less than the range above and the support content exceeds this range, the amount of a Group 10 metal element as an effective ingredient of catalyst is insufficient, failing in obtaining a high hydrogenation effect, and if the content of the Group 10 metal element component exceeds the range above and the support content is less than this range, due to reduction in the catalyst strength, it is also impossible to obtain a high hydrogenation efficiency.

The solid catalyst for use in the present invention may contain other metal elements as long as it contains a metal element belonging to Groups 9 to 11 of the periodic table. However, the solid catalyst for use in the present invention does not contain ruthenium. Examples of other metal elements which may be contained include chromium, manganese, zinc, magnesium, sodium, rhenium, and calcium, and among these, it is preferred to contain magnesium. This metal element may also be contained in the form of a metal element itself, an oxide, a hydroxide or other various salts.

In the case where the solid catalyst for use in the present invention contains a metal element (except for ruthenium) other than the metal element belonging to Groups 9 to 11 of the periodic table, such as magnesium oxide, the content thereof in the solid catalyst (here, when the other metal element is in the form of a metal oxide or the like, the content of the metal component other than the metal element belonging to Groups 9 to 11 of the periodic table is the content as the metal oxide or the like) is preferably from 0.1 to 20 wt %, more preferably from 0.5 to 15 wt %, still more preferably from 1 to 10 wt %.

The catalytic activity can be enhanced by using such another metal component in combination, but if the content thereof is too small, a sufficient combination effect cannot be obtained, whereas if the content is too large, the contents of the metal element component of Groups 9 to 11 of the periodic table and the support are relatively reduced and in turn, the hydrogenation catalyst activity inherent to the solid catalyst according to the present invention and the selectivity may be impaired. In particular, the rate at which 1,4-butanediol disappears due to its conversion to a high-boiling-point byproduct rises.

Incidentally, the solid catalyst is not particularly limited in its shape or size and may be in the form of powder, granule or particle and furthermore, may be a molded article such as pellet. Also, the size of the solid catalyst is arbitrary, but in the case of, for example, a pellet-shaped solid catalyst, the diameter is preferably from 1 to 20 mm, and the thickness is preferably from 1 to 20 mm.

Such a solid catalyst can be produced by a method of, for example, dipping a support in an aqueous solution of a metal salt of Groups 9 to 11 of the periodic table to carry the metal salt and thereafter, subjecting the support to firing and, if desired, molding. The reaction temperature at the time of performing hydrogenation in the present invention is preferably from 0 to 200° C., more preferably from 30 to 150° C., still more preferably from 40 to 120° C. If this temperature is too high, catalyst deterioration is accelerated. Furthermore, the amount of a high-boiling byproduct increases. If the reaction temperature is too low, the reaction scarcely proceeds.

The hydrogen gas pressure in hydrogenation is, as a gauge pressure, from 0.1 to 100 MPa, preferably from 0.5 to 10 MPa, more preferably from 1 to 6 MPa. If this pressure is too low, the reaction rate is low and the productivity decreases. If the pressure is too high, the pressure resistance load of the reactor and the compressor load are increased and the construction cost greatly rises.

Also, the residence time of the reaction solution is, on the empty column basis, preferably 5 minutes or more, more preferably 10 minutes or more, still more preferably 30 minutes or more, and is preferably 100 hours or less, more preferably 50 hours or less, still more preferably 10 hours or less. If the residence time is too short, the reaction scarcely proceeds, whereas if the residence time is too long, the catalyst-packed bed becomes long and large and the economical efficiency is greatly reduced due to increase in the equipment cost of the reactor and increase in the catalyst amount.

As determined from the above-described residence time on the empty column basis, the amount of catalyst packed is, based on the flow rate of the introduced liquid per minute, preferably 5 times in volume or more, more preferably 10 times in volume or more, still more preferably 30 times in volume, and is preferably 6,000 times in volume or less, more preferably 3,000 times in volume or less, still more preferably 600 times in volume or less. If the amount of catalyst packed is too small, the reaction scarcely proceeds, whereas if the amount of catalyst packed is too large, the catalyst cost increases and the economical efficiency is greatly reduced.

As for the reaction mode, all of hydrogenation reactors of a general packed bed type using various solid catalysts, such as fixed bed, trickle bed and multi-tubular system, may be used, but either a fixed bed reactor or a tickle bed reactor is preferred. As the reactor, one reactor may be used, or a plurality of reactors may be used.

The production method of 1,4-butanediol of the present invention is characterized in that at the time of flowing crude 1,4-BG containing an unsaturated compound having a carbon number of 4 into a packed bed filled with a solid catalyst obtained by loading a metal element belonging to Groups 9 to 11 of the periodic table on a support, thereby converting the unsaturated compound in the crude 1,4BG into a corresponding hydride to produce 1,4-butanediol reduced in the concentration of an unsaturated compound having a carbon number of 4, the concentration of a nitrogen component in the packed bed is from 1 ppm by weight to 1 wt % in terms of nitrogen atom. The solid catalyst used for hydrogenation, the nitrogen component and the reaction conditions in hydrogenation are as illustrated above in the description of the production method of a hydride of the present invention.

The concentration of an unsaturated compound having a carbon number of 4 in crude 1,4BG to which the production method of the present invention is applied is 0.01 wt % or more, preferably 0.1 wt % or more, more preferably 1.0 wt % or more. As this value is larger, the effects of the present invention become higher, and the separation load of an unsaturated compound having a carbon number of 4 in the process of producing 1,4-butanediol tends to be reduced. On the other hand, the concentration of an unsaturated compound having a carbon number of 4 in crude 1,4-butanediol is 10 wt % or less, preferably 7 wt % or less, more preferably 5 wt % or less. As this value is smaller, the load such as pressure, catalyst amount and reaction temperature in the hydrogenation reaction of the present invention can be likely to be reduced.

In the production method of 1,4-butanediol of the present invention, crude 1,4-butanediol is preferably flowed into a packed bed filled with a solid catalyst to thereby bring the unsaturated compound having a carbon number of 4 in the crude 1,4-butanediol into contact with a solid catalyst. At this time, the concentration of the nitrogen component contained in crude 1,4-butanediol flowing in the packed bed must be from 1 ppm by weight to 1 wt % in terms of nitrogen atom. The concentration is preferably from 2 ppm by weight to 0.1 wt %, more preferably from 3 to 500 ppm by weight. If the nitrogen atom concentration exceeds this range, the effect on the acceleration of deterioration rate becomes greater than on the improvement of catalyst life, and if the concentration is less than the range above, the effect of improving the catalyst life is scarcely brought out.

EXAMPLES

The present invention is described in greater detail below by referring to Examples, but the present invention is not limited to these Examples as long as the gist of the present invention is observed. Incidentally, the analysis was performed by gas chromatography according to an internal standard method. At this time, n-dodecane was used as the internal standard, and GC-14A (column: DB-WAX) manufactured by Shimadzu Corporation was used for the gas chromatography.

Example 1

A 500 cc-volume glass-made chromatograph tube with a jacket capable of flowing warm water and thereby heating the tube was filled with 300 cc of an anion exchange resin (Diaion (registered trademark), model: WA20, produced by Mitsubishi Chemical Corporation), and 1,4-butanediol containing 1,4-dihydroxy-2-butene was flowed from the top of the glass-made chromatograph tube at 215 g/hr. At this time, the temperature on contacting 1,4-butanediol with the anion exchange resin was 55° C., and the pressure was atmospheric pressure. Incidentally, the liquid after flowing contained a nitrogen component in an amount of 12 ppm by weight in terms of nitrogen atom, and both the chloride ion concentration and the sulfur concentration were below the detection limit.

This 1,4-butanediol containing 10.65 wt % of 1,4-dihydroxy-2-butene after the anion exchange resin treatment was subjected to a hydrogenation reaction by using a flow reaction apparatus having a reactor volume of 120 cc. For the catalyst, 100 cc of a pellet-shaped diatomaceous earth-supported nickel-chromium catalyst (amount supported: 12 wt % of nickel, 1.5 wt % of chromium) was used. Here, the reactor of the flow reaction apparatus was filled with the solid catalyst by providing a filter manufactured by SUS, a glass bead bed, a solid catalyst bed, a glass bead bed, and a filter manufactured by SUS in this order.

The reaction conditions of the hydrogenation reaction were set to a reaction temperature of 100° C. and a reaction pressure of 3.5 MPaG. Also, the flow rate of the reaction solution was set to 50 cc/h. The results are shown in Table 1.

Example 2

10 g of an anion exchange resin (Diaion (registered trademark), model: WA20, produced by Mitsubishi Chemical Corporation) was added to 100 g of 1,4-butanediol containing 10.0 wt % of 1,4-dihydroxy-2-butene (chloride ion concentration: 70 ppm, sulfur concentration: below detection limit, nitrogen concentration: below detection limit), and the mixture was stirred at room temperature for 2 hours.

After separating the anion exchange resin by filtration, 4.0 g of the resulting solution (nitrogen concentration: 14 ppm) and 1.0 g of a pellet-shaped diatomaceous earth-supported nickel-chromium catalyst (amount supported: 12 wt % of nickel, 1.5 wt % of chromium) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol (nitrogen concentration: 14 ppm) containing 10.0 wt % of 1,4-dihydroxy-2-butene and after nitrogen purging, the hydrogen pressure was set to 0.99 MPaG. This autoclave was shaken in an oil bath at 140° C. for 4 hours.

The solution after the completion of reaction was analyzed, as a result, the conversion rate of 1,4-dihydroxy-2-butene was 94.2%.

Example 3

Tributylamine was added to 100 g of 1,4-butanediol containing 10.0 wt % of 1,4-dihydroxy-2-butene (chloride ion concentration: 70 ppm, sulfur concentration: below detection limit, nitrogen concentration: below detection limit) to have a concentration of 1 ppm in terms of nitrogen atom, and 4.0 g of this solution (nitrogen concentration: 1 ppm) and 1.0 g of a pellet-shaped diatomaceous earth-supported nickel-chromium catalyst (amount supported: 12 wt % of nickel, 1.5 wt % of chromium) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol containing tributylamine at a concentration of 1 ppm in terms of nitrogen atom and 10.0 wt % of 1,4-dihydroxy-2-butene and after nitrogen purging, the hydrogen pressure was set to 0.99 MPaG. This autoclave was shaken in an oil bath at 140° C. for 4 hours.

The solution after the completion of reaction was analyzed, as a result, the conversion rate of 1,4-dihydroxy-2-butene was 97.6%.

Example 4

The reaction was performed entirely in the same manner as in Example 3 except that 1,4-butanediol containing tributylamine at a concentration of 700 ppm in terms of nitrogen atom and 10.0 wt % of 1,4-dihydroxy-2-butene was used in place of 1,4-butanediol containing tributylamine at a concentration of 1 ppm in terms of nitrogen atom and 10.0 wt % of 1,4-dihydroxy-2-butene.

The solution after the completion of reaction was analyzed, as a result, the conversion rate of 1,4-dihydroxy-2-butene was 98.2%.

Example 5

Tributylamine was added to 100 g of 1,4-butanediol containing 10.0 wt % of 1,4-dihydroxy-2-butene (chloride ion concentration: 70 ppm, sulfur concentration: 2 ppm, nitrogen concentration: below detection limit) to have a concentration of 5 ppm in terms of nitrogen atom, and 4.0 g of this solution (nitrogen concentration: 1 ppm) and 1.0 g of a pellet-shaped silica-supported nickel catalyst (amount supported: 17 wt % of nickel, 55 wt % of nickel oxide) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol containing tributylamine at a concentration of 5 ppm in terms of nitrogen atom and 10.0 wt % of 1,4-dihydroxy-2-butene and after nitrogen purging, the hydrogen pressure was set to 0.99 MPaG. This autoclave was shaken in an oil bath at 140° C. for 1 hour.

The solution after the completion of reaction was analyzed, as a result, the conversion rate of 1,4-dihydroxy-2-butene was 90.3%.

Example 6

Tributylamine was added to 100 g of 1,4-butanediol containing 10.0 wt % of 1,4-dihydroxy-2-butene (chloride ion concentration: 70 ppm, sulfur concentration: 2 ppm, nitrogen concentration: below detection limit) to have a concentration of 5 ppm in terms of nitrogen atom, and 4.0 g of this solution (nitrogen concentration: 1 ppm) and 1.0 g of a pellet-shaped silica-supported palladium catalyst (amount supported: 2 wt % of palladium) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol containing tributylamine at a concentration of 5 ppm in terms of nitrogen atom and 10.0 wt % of 1,4-dihydroxy-2-butene and after nitrogen purging, the hydrogen pressure was set to 0.99 MPaG. This autoclave was shaken in an oil bath at 100° C. for 1 hour.

The solution after the completion of reaction was analyzed, as a result, the conversion rate of 1,4-dihydroxy-2-butene was 36.8%.

Example 7

Tributylamine was added to 100 g of 1,4-butanediol containing 10.0 wt % of methyl vinyl ketone (chloride ion concentration: below detection limit, sulfur concentration: 2 ppm, nitrogen concentration: below detection limit) to have a concentration of 5 ppm in terms of nitrogen atom, and 4.0 g of this solution (nitrogen concentration: 1 ppm) and 1.0 g of a pellet-shaped diatomaceous earth-supported nickel-chromium catalyst (amount supported: 12 wt % of nickel, 1.5 wt % of chromium)) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol containing tributylamine at a concentration of 5 ppm in terms of nitrogen atom and 2.0 wt % of methyl vinyl ketone and after nitrogen purging, the hydrogen pressure was set to 0.99 MPaG. This autoclave was shaken in an oil bath at 100° C. for 1 hour.

The solution after the completion of reaction was analyzed, as a result, the conversion rate of 1,4-dihydroxy-2-butene was 38.6%.

Example 8

Tributylamine was added to 100 g of 1,4-butanediol containing 10.0 wt % of crotonaldehyde (chloride ion concentration: below detection limit, sulfur concentration: 2 ppm, nitrogen concentration: below detection limit) to have a concentration of 5 ppm in terms of nitrogen atom, and 4.0 g of this solution (nitrogen concentration: 1 ppm) and 1.0 g of a pellet-shaped diatomaceous earth-supported nickel-chromium catalyst (amount supported: 12 wt % of nickel, 1.5 wt % of chromium)) were put in a 50 cc glass vessel and heated in an oil bath at 140° C. for 5 hours.

A 100 cc stainless steel-made autoclave was charged with 1 g of the heat-treated catalyst and 40.0 g of the 1,4-butanediol containing tributylamine at a concentration of 5 ppm in terms of nitrogen atom and 2.0 wt % of crotonaldehyde and after nitrogen purging, the hydrogen pressure was set to 0.99 MPaG. This autoclave was shaken in an oil bath at 60° C. for 1 hour.

The solution after the completion of reaction was analyzed, as a result, the conversion rate of 1,4-dihydroxy-2-butene was 63.4%.

Comparative Example 1

The hydrogenation reaction was performed entirely under the same conditions as in Example 1 except that the raw material solution of 1,4-butanediol containing 1,4-dihydroxy-2-butene (chloride ion concentration: 70 ppm, sulfur concentration: below detection limit) was not flowed to the anion exchange resin. The results are shown in Table 1.

Comparative Example 2

The reaction was performed entirely in the same manner as in Example 3 except that tributylamine was not added to 1,4-butanediol containing 10.0 wt % of 1,4-dihydroxy-2-butene (chloride ion concentration: 70 ppm, sulfur concentration: below detection limit, nitrogen concentration: below detection limit).

The solution after the completion of reaction was analyzed, as a result, the conversion rate of 1,4-dihydroxy-2-butene was 90.2%.

Comparative Example 3

The reaction was performed entirely in the same manner as in Example 5 except that tributylamine was not added to 1,4-butanediol containing 10.0 wt % of 1,4-dihydroxy-2-butene (chloride ion concentration: 70 ppm, sulfur concentration: 2 ppm, nitrogen concentration: below detection limit).

The solution after the completion of reaction was analyzed, as a result, the conversion rate of 1,4-dihydroxy-2-butene was 88.2%.

Comparative Example 4

The reaction was performed entirely in the same manner as in Example 6 except that tributylamine was not added to 1,4-butanediol containing 10.0 wt % of 1,4-dihydroxy-2-butene (chloride ion concentration: 70 ppm, sulfur concentration: 2 ppm, nitrogen concentration: below detection limit).

The solution after the completion of reaction was analyzed, as a result, the conversion rate of 1,4-dihydroxy-2-butene was 30.5%.

Comparative Example 5

The reaction was performed entirely in the same manner as in Example 7 except that tributylamine was not added to 1,4-butanediol containing methyl vinyl ketone (chloride ion concentration: below detection limit, sulfur concentration: 2 ppm, nitrogen concentration: below detection limit).

The solution after the completion of reaction was analyzed, as a result, the conversion rate of methyl vinyl ketone was 34.1%.

Comparative Example 6

The reaction was performed entirely in the same manner as in Example 8 except that tributylamine was not added to 1,4-butanediol containing crotonaldehyde (chloride ion concentration: below detection limit, sulfur concentration: 2 ppm, nitrogen concentration: below detection limit).

The solution after the completion of reaction was analyzed, as a result, the conversion rate of crotonaldehyde was 56.5%.

Reference Example 1

A 100 cc stainless steel-made autoclave was charged with 1 g of a pellet-shaped diatomaceous earth-supported nickel-chromium catalyst (amount supported: 12 wt % of nickel, 1.5 wt % of chromium) and 40.0 g of the 1,4-butanediol containing 10.0 wt % of 1,4-dihydroxy-2-butene (chloride ion concentration: 70 ppm, sulfur concentration: below detection limit, nitrogen concentration: below detection limit) and after nitrogen purging, the hydrogen pressure was set to 0.99 MPaG. This autoclave was shaken in an oil bath at 140° C. for 4 hours.

The solution after the completion of reaction was analyzed, as a result, the conversion rate of 1,4-dihydroxy-2-butene was 98.2%.

Reference Example 2

A 100 cc stainless steel-made autoclave was charged with 1.0 g of a pellet-shaped silica-supported nickel catalyst (amount supported: 17 wt % of nickel, 55 wt % of nickel oxide) and 40.0 g of 1,4-butanediol containing 10.0 wt % of 1,4-dihydroxy-2-butene (chloride ion concentration: 70 ppm, sulfur concentration: below detection limit, nitrogen concentration: below detection limit) and after nitrogen purging, the hydrogen pressure was set to 0.99 MPaG. This autoclave was shaken in an oil bath at 140° C. for 1 hour.

The solution after the completion of reaction was analyzed, as a result, the conversion rate of 1,4-dihydroxy-2-butene was 97.6%.

Reference Example 3

A 100 cc stainless steel-made autoclave was charged with 1.0 g of a pellet-shaped silica-supported palladium catalyst (amount supported: 2 wt % of palladium) and 40.0 g of 1,4-butanediol containing 10.0 wt % of 1,4-dihydroxy-2-butene (chloride ion concentration: 70 ppm, sulfur concentration: below detection limit, nitrogen concentration: below detection limit) and after nitrogen purging, the hydrogen pressure was set to 0.99 MPaG. This autoclave was shaken in an oil bath at 100° C. for 1 hour.

The solution after the completion of reaction was analyzed, as a result, the conversion rate of 1,4-dihydroxy-2-butene was 42.7%.

Reference Example 4

A 100 cc stainless steel-made autoclave was charged with 1 g of a pellet-shaped diatomaceous earth-supported nickel-chromium catalyst (amount supported: 12 wt % of nickel, 1.5 wt % of chromium) and 40.0 g of 1,4-butanediol containing 2.0 wt % of methyl vinyl ketone (chloride ion concentration: 70 ppm, sulfur concentration: 2 ppm, nitrogen concentration: below detection limit) and after nitrogen purging, the hydrogen pressure was set to 0.99 MPaG. This autoclave was shaken in an oil bath at 100° C. for 1 hour.

The solution after the completion of reaction was analyzed, as a result, the conversion rate of methyl vinyl ketone was 41.1%.

Reference Example 5

A 100 cc stainless steel-made autoclave was charged with 1 g of a pellet-shaped diatomaceous earth-supported nickel-chromium catalyst (amount supported: 12 wt % of nickel, 1.5 wt % of chromium) and 40.0 g of 1,4-butanediol containing 2.0 wt % of crotonaldehyde (chloride ion concentration: 70 ppm, sulfur concentration: 2 ppm, nitrogen concentration: below detection limit) and after nitrogen purging, the hydrogen pressure was set to 0.99 MPaG. This autoclave was shaken in an oil bath at 60° C. for 1 hour.

The solution after the completion of reaction was analyzed, as a result, the conversion rate of crotonaldehyde was 65.5%.

TABLE 1

| | Raw Material/14BG Solution | | | Treatment of Raw Material | | |
|---|---|---|---|---|---|---|
| | Unsaturated Compound | Raw Material Cl Concentration ppm | Raw Material S Concentration ppm | N Compound | N Concentration after Treatment ppm | Heat Treatment of Catalyst |
| Example 1 | 1,4-butenediol | 70 | below DT | WA20 | 12 | 100° C., 300 hour |
| Example 2 | 1,4-butenediol | 70 | below DT | WA20 | 14 | 140° C., 5 h heating |
| Example 3 | 1,4-butenediol | 70 | below DT | tributylamine | 1 | 140° C., 5 h heating |
| Example 4 | 1,4-butenediol | 70 | below DT | tributylamine | 700 | 140° C., 5 h heating |
| Example 5 | 1,4-butenediol | 70 | 2 | tributylamine | 5 | 140° C., 5 h heating |
| Example 6 | 1,4-butenediol | 70 | 2 | tributylamine | 5 | 140° C., 5 h heating |
| Example 7 | methyl vinyl ketone | — | 2 | tributylamine | 5 | 140° C., 5 h heating |
| Example 8 | crotonaldehyde | — | 2 | tributylamine | 5 | 140° C., 5 h heating |
| Comparative Example 1 | 1,4-butenediol | 70 | below DT | — | below DT | 100° C., 300 hours |
| Comparative Example 2 | 1,4-butenediol | 70 | below DT | — | below DT | 140° C., 5 h heating |
| Comparative Example 3 | 1,4-butenediol | 70 | 2 | — | below DT | 140° C., 5 h heating |
| Comparative Example 4 | 1,4-butenediol | 70 | 2 | — | below DT | 140° C., 5 h heating |
| Comparative Example 5 | methyl vinyl ketone | — | 2 | — | below DT | 140° C., 5 h heating |
| Comparative Example 6 | crotonaldehyde | — | 2 | — | below DT | 140° C., 5 h heating |
| Reference Example 1 | 1,4-butenediol | 70 | below DT | — | below DT | none (fresh catalyst) |
| Reference Example 2 | 1,4-butenediol | 70 | 2 | — | below DT | none (fresh catalyst) |
| Reference Example 3 | 1,4-butenediol | 70 | 2 | — | below DT | none (fresh catalyst) |
| Reference Example 4 | methyl vinyl ketone | — | 2 | — | below DT | none (fresh catalyst) |
| Reference Example 5 | crotonaldehyde | — | 2 | — | below DT | none (fresh catalyst) |

| | | | Evaluation Conditions | | | | |
|---|---|---|---|---|---|---|---|
| | Catalyst | Reaction Mode | Concentration of Raw Material (BG solvent) | Reaction Temperature ° C. | Reaction Pressure MPaG | Reaction Time hr | Conversion Rate (%) |
| Example 1 | Ni/diatomaceous earth | flow | 10 wt % | 100 | 3.5 | 2 | 98.3 |
| Example 2 | Ni/diatomaceous earth | batch | 10 wt % | 140 | 0.99 | 4 | 94.2 |
| Example 3 | Ni/diatomaceous earth | batch | 10 wt % | 140 | 0.99 | 4 | 97.6 |
| Example 4 | Ni/diatomaceous earth | batch | 10 wt % | 140 | 0.99 | 4 | 98.2 |
| Example 5 | Ni/SiO2 | batch | 10 wt % | 140 | 0.99 | 1 | 90.3 |
| Example 6 | 2% Pd/SiO2 | batch | 10 wt % | 100 | 0.99 | 1 | 36.8 |
| Example 7 | Ni/diatomaceous earth | batch | 2 wt % | 100 | 0.99 | 1 | 38.6 |
| Example 8 | Ni/diatomaceous earth | batch | 2 wt % | 60 | 0.99 | 1 | 63.4 |
| Comparative Example 1 | Ni/diatomaceous earth | flow | 10 wt % | 100 | 3.5 | 2 | 76.3 |
| Comparative Example 2 | Ni/diatomaceous earth | batch | 10 wt % | 140 | 0.99 | 4 | 90.2 |
| Comparative Example 3 | Ni/SiO2 | batch | 10 wt % | 140 | 0.99 | 1 | 88.2 |
| Comparative Example 4 | 2% Pd/SiO2 | batch | 10 wt % | 100 | 0.99 | 1 | 30.5 |
| Comparative Example 5 | Ni/diatomaceous earth | batch | 2 wt % | 100 | 0.99 | 1 | 34.1 |
| Comparative | Ni/diatomaceous earth | batch | 2 wt % | 60 | 0.99 | 1 | 56.5 |

TABLE 1-continued

| | | | | | | | |
|---|---|---|---|---|---|---|---|
| Example 6 | | | | | | | |
| Reference Example 1 | Ni/diatomaceous earth | batch | 10 wt % | 140 | 0.99 | 4 | 98.2 |
| Reference Example 2 | Ni/SiO2 | batch | 10 wt % | 140 | 0.99 | 1 | 97.6 |
| Reference Example 3 | 2% Pd/SiO2 | batch | 10 wt % | 100 | 0.99 | 1 | 42.7 |
| Reference Example 4 | Ni/diatomaceous earth | batch | 2 wt % | 100 | 0.99 | 1 | 41.1 |
| Reference Example 5 | Ni/diatomaceous earth | batch | 2 wt % | 60 | 0.99 | 1 | 65.5 |

*DT: detection limit

According to the present invention, the catalyst life can be improved when a nitrogen-containing component exists, as compared with the case where a nitrogen-containing component is not present.

While the invention has been described in detail and with reference to specific embodiments thereof, it will be apparent to one skilled in the art that various changes and modifications can be made therein without departing from the spirit and scope thereof. This application is based on a Japanese patent application filed on Jul. 20, 2011 (Application No. 2011-159105), a Japanese patent application filed on Jul. 28, 2011 (Application No. 2011-165937) and a Japanese patent application filed on Nov. 2, 2011 (Application No. 2011-241574), the content thereof being incorporated herein by reference.

The invention claimed is:

1. A method for producing a hydride having a carbon number of 4, comprising contacting, in liquid phase, an unsaturated compound having a total carbon number of 4 as a raw material with a solid catalyst obtained by loading a metal element belonging to Groups 9 to 11 of the long periodic table on a support, and performing hydrogenation to continuously produce a corresponding hydride having a carbon number of 4, wherein the hydrogenation is performed in the presence of a solvent comprising 1,4-butanediol having a nitrogen component concentration of 1 ppm by weight to 1 wt % in terms of nitrogen atom.

2. The method for producing a hydride having a carbon number of 4 according to claim 1, wherein the support is at least one member of silica and diatomaceous earth.

3. The method for producing a hydride having a carbon number of 4 according to claim 1, wherein the unsaturated compound having a carbon number of 4 is 1,4-dihydroxy-2-butene and the corresponding hydride having a carbon number of 4 is at least one member of 2, -hydroxytetrahydrofuran and 1,4-butanediol.

4. A method for producing 1,4-butanediol comprising flowing crude 1,4-butanediol containing an unsaturated compound having a total carbon number of 4 into a packed bed filled with a solid catalyst obtained by loading a metal element belonging to Groups 9 to 11 of the long periodic table on a support, and converting the unsaturated compound having a carbon number of 4 into a corresponding hydride having a carbon number of 4 to obtain 1,4-butanediol reduced in the concentration of an unsaturated compound having a carbon number of 4, wherein the concentration of a nitrogen component contained in the crude 1,4-butanediol in the packed bed is from 1 ppm by weight to 1 wt % in terms of nitrogen atom.

5. The method for producing a hydride having a carbon number of 4 according to claim 1, wherein the metal element belonging to Groups 9 to 11 of the long periodic table is a metal element belonging to Group 10 of the long periodic table.

6. The method according to claim 4, wherein the metal element belonging to Groups 9 to 11 of the long periodic table is a metal element belonging to Group 10 of the long periodic table.

7. The method for producing a hydride having a carbon number of 4 according to claim 5, wherein the metal element is nickel or palladium.

8. The method according to claim 6, wherein the metal element is nickel or palladium.

9. The method for producing a hydride having a carbon number of 4 according to claim 1, wherein the nitrogen component is an eluate of an anionic exchange resin having a primary amine polyethylene diamine skeleton having an N—H bond.

10. The method according to claim 4, wherein the nitrogen component is an eluate of an anionic exchange resin having a primary amine polyethylene diamine skeleton having an N—H bond.

11. The method for producing a hydride having a carbon number of 4 according to claim 1, wherein the unsaturated compound having a total carbon number of 4 is present in an amount of 0.1 to 30 wt %.

12. The method for producing a hydride having a carbon number of 4 according to claim 1, wherein the unsaturated compound having a total carbon number of 4 is present in an amount of 0.5 to 20 wt %.

13. The method for producing a hydride having a carbon number of 4 according to claim 1, wherein the solvent comprises from 50 to 99.99 wt % of 1,4 butanediol.

14. The method for producing a hydride having a carbon number of 4 according to claim 1, wherein the nitrogen component concentration is 3 to 500 ppm by weight in terms of nitrogen atom.

15. The method according to claim 4, wherein the nitrogen component concentration is 3 to 500 ppm by weight in terms of nitrogen atom.

16. The method for producing a hydride having a carbon number of 4 according to claim 1, wherein the nitrogen component is tributylamine.

17. The method according to claim 4, wherein the nitrogen component is tributylamine.

18. The method for producing a hydride having a carbon number of 4 according to claim 1, wherein the method is a continuous method.

* * * * *